US008765415B2

(12) United States Patent
Arunakumari et al.

(10) Patent No.: US 8,765,415 B2
(45) Date of Patent: Jul. 1, 2014

(54) METHODS FOR ENHANCED PROTEIN PRODUCTION (75) Inventors: Alahari Arunakumari, Pennington, NJ (US); Xiao-Ping Dai, Flemington, NJ (US); Javier Garcia, Palmerton, NJ (US); Richard P. Martel, Allentown, PA (US)

(73) Assignee: Medarex, L.L.C., Princeton, NJ (US)

( * ) Notice: Subject to any disclaimer, the term of this patent is extended or adjusted under 35 U.S.C. 154(b) by 0 days.

(21) Appl. No.: 13/510,372

(22) PCT Filed: Nov. 17, 2010

(86) PCT No.: PCT/US2010/056924
§ 371 (c)(1),
(2), (4) Date: Jun. 14, 2012

(87) PCT Pub. No.: WO2011/062926
PCT Pub. Date: May 26, 2011

(65) Prior Publication Data
US 2013/0017577 A1    Jan. 17, 2013

Related U.S. Application Data (60) Provisional application No. 61/261,886, filed on Nov. 17, 2009.

(51) Int. Cl.
*C12P 21/02* (2006.01)
*A61K 38/00* (2006.01)

(52) U.S. Cl.
USPC .................................................... 435/71.1

(58) Field of Classification Search
USPC ............... 435/71.1, 41, 325, 383; 210/296
IPC ............................... C12P 21/02; A61K 38/00
See application file for complete search history.

(56) References Cited

U.S. PATENT DOCUMENTS

| | | | |
|---|---|---|---|
| 4,399,216 A | 8/1983 | Axel et al. |
| 4,816,567 A | 3/1989 | Cabilly et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,476,996 A | 12/1995 | Wilson et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,762 A | 12/1997 | Queen et al. |
| 5,698,767 A | 12/1997 | Wilson et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,172,197 B1 | 1/2001 | McCafferty et al. |
| 6,180,370 B1 | 1/2001 | Queen et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Grigg et al. |
| 2008/0206819 A1* | 8/2008 | Tsao et al. .............. 435/70.3 |
| 2009/0042253 A1* | 2/2009 | Hiller ...................... 435/70.3 |
| 2009/0068705 A1* | 3/2009 | Drapeau et al. ......... 435/69.3 |
| 2011/0207225 A1* | 8/2011 | Mehta et al. .............. 435/455 |

FOREIGN PATENT DOCUMENTS

| | | |
|---|---|---|
| WO | WO 92/03918 | 3/1992 |
| WO | WO 93/08207 | 4/1993 |
| WO | WO 93/12227 | 6/1993 |
| WO | WO 94/25585 | 11/1994 |

(Continued)

OTHER PUBLICATIONS

Wlaschin K. et al. Fedbatch Culture and Dynamic Nutirent Feeding. Adv biochem Engineering Biotechnology 101:43-74, 2006.*
Bird, R.E. et al., "Single-Chain Antigen-Binding Proteins", Science, vol. 242, pp. 423-426 (1988).
Chen, J. et al., "B cell development in mice that lack one or both immunoglobulin κ light chain genes", The EMBO Journal, vol. 12, No. 3, pp. 821-830 (1993).
Chen, J. et al., "Immunoglobulin gene rearrangement in B cell deficient mice generated by targeted deletion of the $J_H$ locus", International Immunology, vol. 5, No. 6, pp. 647-656 (1993).
Choi, T.K. et al., "Transgenic mice containing a human heavy chain immunoglobulin gene fragment cloned in a yeast artificial chromosome", Nature Genetics, vol. 4, pp. 117-123, and a correction p. 320 (1993).
Clackson, T. et al., "Making antibody fragments using phage display libraries", Nature, vol. 352, pp. 624-628 (1991).

(Continued)

*Primary Examiner* — Ralph Gitomer
(74) *Attorney, Agent, or Firm* — Z. Angela Guo (57) ABSTRACT

The present invention provides a method of increasing protein production in a cell culture by growing cells that produce the protein (e.g., the growth phase) in a perfusion cell culture to a high cell density (i.e., at least above about $40 \times 10^6$ cells/N mL) and then switching to a protein production phase, wherein the cells are cultured in a fed-batch cell culture. The present invention further provides a method for clarifying a protein from a cell culture by adjusting the pH of the cell culture to below neutral pH (i.e., below a pH of 7) and settling the cell culture, such that the cell culture separates to form a supernatant layer and a cell-bed layer, wherein the protein is in the supernatant layer.

13 Claims, 7 Drawing Sheets

(56) References Cited

FOREIGN PATENT DOCUMENTS

| WO | WO 96/40918 | 12/1996 |
|---|---|---|
| WO | WO 97/13852 | 4/1997 |
| WO | WO 98/24884 | 6/1998 |
| WO | WO 99/45962 | 9/1999 |
| WO | WO 01/14424 | 3/2001 |
| WO | WO 02/43478 | 6/2002 |
| WO | WO 2009/023562 | 2/2009 |

OTHER PUBLICATIONS

Fiers, W. et al., Complete nucleotide sequence of SV40 DNA, Nature, vol. 273, pp. 113-120 (1978).
Fishwild, D.M. et al., "High-avidity human IgGκ monoclonal antibodies from a novel strain of minilocus transgenic mice", Nature Biotechnology, vol. 14, pp. 845-851 (1996).
Graham, F.L. et al., "Characteristics of a Human Cell Line Transformed by DNA from Human Adenovirus Type 5", Journal Gen. Virology, vol. 36, pp. 59-72 (1977).
Huston, J.S. et al., "Protein engineering of antibody binding sites: Recovery of specific activity in an anti-digoxin single-chain Fv analogue produced in *Escherichia coli*", Proc. Natl. Acad. Sci. USA, vol. 85, pp. 5879-5883 (1988).
Jones, P.T. et al., "Replacing the complementarity-determining regions in a human antibody with those from a mouse", Nature, vol. 321, pp. 522-525 (1986).
Karin, M. et al., "Human metallothionein genes—primary structure of the metallothionein-II gene and a related processed gene", Nature, vol. 299, pp. 797-802 (1982).
Keown, W.A. et al., "Methods for Introducing DNA into Mammalian Cells", Methods in Enzymology, vol. 185, pp. 527-537 (1990).
Köhler, G. et al., "Continuous cultures of fused cells secreting antibody of predefined specificity", Nature, vol. 256, pp. 495-497 (1975).
Kolhekar, A.S. et al., "Peptidylglycine α-Hydroxylating Monooxygenase: Active Site Residues, Disulfide Linkages, and a Two-Domain Model of the Catalytic Core", Biochemistry, vol. 36, pp. 10901-10909 (1997).
Konstantinov, K. et al., "The "Push-to-Low" Approach for Optimization of High-Density Perfusion Cultures of Animal Cells", Adv. Biochem Engin/Biotechnology, vol. 101, pp. 75-98 (2006).
Kostelny, S.A. et al., "Formation of a Bispecific Antibody by the Use of Leucine Zippers", The Journal of Immunology, vol. 148, No. 5, pp. 1547-1553 (1992).
Lee, J. et al., "Control of fed-batch fermentations", Biotechnology Advances, vol. 17, pp. 29-48 (1999).
Mansour, S.L. et al., "Disruption of the proto-oncogene int-2 in mouse embryo-derived stem cells: a general strategy for targeting mutations to non-selectable genes", Nature, vol. 336, pp. 348-352 (1988).
Marks, J.D. et al., "By-passing Immunization—Human Antibodies from V-gene Libraries Displayed on Phage", J. Mol. Biol., vol. 222, pp. 581-597 (1991).

Mather, J.P. et al., "Culture of Testicular Cells in Hormone-Supplemented Serum-Free Medium", Annals New York Academy of Sciences, vol. 383, pp. 44-68 (1982).
Mather, J.P., "Establishment and Characterization of Two Distinct Mouse Testicular Epithelial Cell Lines", Biology of Reproduction, vol. 23, pp. 243-252 (1980).
Morrison, S.L. et al., "Chimeric human antibody molecules: Mouse antigen-binding domains with human constant region domains", Proc. Natl. Acad. Sci. USA, vol. 81, pp. 6851-6855 (1984).
Presta, L.G., "Antibody engineering", Current Opinion in Structural Biology, vol. 2, pp. 593-596 (1992).
Riechmann, L., et al. "Reshaping human antibodies for therapy", Nature, vol. 332, pp. 323-327 (1988).
Schumpp, B. et al., "Optimization of culture conditions for high cell density proliferation of HL-60 human promyelocytic leukemia cells", Journal of Cell Science, vol. 97, pp. 639-649 (1990).
Songsivilai, S. et al., "Bispecific antibody: a tool for diagnosis and treatment of disease", Clin. Exp. Immunol., vol. 79, pp. 315-321 (1990).
Sun, X. et al., "High-Density Transient Gene Expression in Suspension-Adapted 293 EBNA1 Cells", Biotechnology and Bioengineering, vol. 99, No. 1, pp. 108-116 (2008).
Taylor, L.D. et al., "A transgenic mouse that expresses a diversity of human sequence heavy and light chain immunoglobulins", Nucleic Acids Research, vol. 20, No. 23, pp. 6287-6295 (1992).
Taylor, L.D. et al., "Human immunoglobulin transgenes undergo rearrangement, somatic mutation and class switching in mice that lack endogenous IgM", International Immunology, vol. 6, No. 4, pp. 579-591 (1994).
Tuaillon, N. et al., "Biased Utilization of $D_{HQ52}$ and $J_H4$ Gene Segments in a Human Ig Transgenic Minilocus Is Independent of Antigenic Selection", Journal of Immunology, vol. 152, pp. 2912-2920 (1994).
Tuaillon, N. et al., "Human immunoglobulin heavy-chain minilocus recombination in transgenic mice: Gene-segment use in μ and γ transcripts", Proc. Natl. Acad. Sci. USA, vol. 90, pp. 3720-3724 (1993).
Urlaub, G. et al., "Effect of Gamma Rays at the Dihydrofolate Reductase Locus: Deletions and Inversions", Somatic Cell and Molecular Genetics, vol. 12, No. 6, pp. 555-566 (1986).
Urlaub, G. et al., "Isolation of Chinese hamster cell mutants deficient in dihydrofolate reductase activity", Proc. Natl. Acad. Sci. USA, vol. 77, No. 7, pp. 4216-4220 (1980).
Ward, E.S. et al., "Binding activities of a repertoire of single immunoglobulin variable domains secreted from *Escherichia coli*", Nature, vol. 341, pp. 544-546 (1989).
Wlaschin, K.F. et al., "Fedbatch Culture and Dynamic Nutrient Feeding", Adv. Biochem Engin/Biotechnol, vol. 101, pp. 43-74, (2006).
Yang, J.D. et al., "Achievement of High Cell Density and High Antibody Productivity by a Controlled-Fed Perfusion Bioreactor Process", Biotechnology and Bioengineering, vol. 69, No. 1, pp. 74-82, (2000).
International Search Report—PCT/US2010/056924, mailed Jun. 8, 2011, (6 pages).

\* cited by examiner

METHODS FOR ENHANCED PROTEIN PRODUCTION

CROSS REFERENCE TO RELATED APPLICATION

This application is a 35 U.S.C. §371 National Stage patent application of International Application PCT/US2010/056924, filed Nov. 17, 2010, which claims the benefit of U.S. Provisional Application No. 61/261,886, filed Nov. 17, 2009, each of which is hereby incorporated by reference in its entirety.

BACKGROUND OF THE INVENTION

Animal cell culture, particularly mammalian cell culture, is commonly used for the expression of recombinantly produced proteins for therapeutic, prophylactic and diagnostic purposes. Although mammalian cell culture methods are preferred over microbial expression systems (e.g., bacterial or yeast expression systems), because they are better suited to express high molecular weight proteins and proteins having complex steric structures, protein expression levels from mammalian cell culture-based systems are generally considerably lower than those from microbial expression systems. While numerous approaches have tried to increase protein expression from mammalian cell culture, these methods have been deficient in optimizing conditions for cell growth, maintaining high cell viability and producing large volumes of high quality protein, thereby limiting their practical application in the biopharmaceutical industry.

As such, there is a need in the art to develop improved large-scale animal cell culture methods for producing and purifying proteins (e.g., antibodies and antibody fragments, peptides, enzymes, growth factors, hormones, interleukins, interferons, and vaccines) to achieve reliable and cost-efficient protein production at high yields.

SUMMARY OF THE INVENTION

In certain embodiments, the present invention provides methods for increasing production of a protein in a cell culture by growing cells that produce the protein in perfusion to a high cell density (e.g., at least to above about $40 \times 10^6$ cells/mL, more preferably above about 60 to $80 \times 10^6$ cells/mL, and most preferably around about $100 \times 10^6$ cells/mL), also referred to herein as "super high density", then switching the cell culture to fed-batch, such that the cells enter a high protein production phase. The present invention is based, at least in part, on the unexpected discovery that it is possible to grow cells in culture to a much higher density than previously thought possible. This, in turn, yields significantly more protein than is typically produced using known cell culture techniques. Specifically, the maximum cell density achieved using known cell cultures techniques is generally thought to be limited by the presence of particular levels of waste products (e.g., lactate, ammonium, etc.), since it is known that such waste products can be toxic to cell growth when they accumulate to critical concentrations (see, for example, Schumpp, B. et al., *J. Cell Sci.*, 7(Pt 4):639-647 (December 1990)). As such, known cell culture techniques often limit the maximum density to which cells are initially grown, so that the cells are not adversely affected by particular concentrations of waste products.

For example, the cell culture method described in WO 2009/023562 relies on lactate levels to signal the maximum cell density that can theoretically be achieved before initiating perfusion cell culture. As taught in WO 2009/023562, cells are grown to a cell density of about 1 million to 9 million cells/mL, which results in a lactate concentration of about 1 g/L to about 6 g/L. According to WO 2009/023562, this signals the optimum time point to begin perfusion. After perfusion, cells are then grown to roughly 5 to 40 million cells/mL and maintained in fed-batch cell culture to yield antibody titers between 8-10 g/L (between days 14-17).

In contrast to such known cell culture methods, no particular level of waste products restricts the density of cell growth according to the methods of the present invention. Instead, it was discovered that when cells are initially grown only in a perfusion cell culture, the cells are able to grow to a much higher cell density (e.g., at least above $40 \times 10^6$ cells/mL) than previously reported for known cell culture techniques, regardless of the presence of waste products. In a particular embodiment, the cells are grown to a density of at least above about $40 \times 10^6$ cells/mL to $60 \times 10^6$ cells/mL, preferably above about $70 \times 10^6$ cells/mL to $90 \times 10^6$ cells/mL, more preferably above about $100 \times 10^6$ to $130 \times 10^6$, and most preferably above about $140 \times 10^6$ to $200 \times 10^6$ cells/mL or more. This "super" high density of cells, in turn, enables the production of significantly higher quantities of protein (e.g., 13.8 g/L at day 6) in a shorter period of time than has been previously reported.

The present invention further provides yet another unexpected advantage over known cell culture techniques in that it optimizes the production of large amounts of high quality protein. For example, in one embodiment, protein harvested according to the methods of the present invention is obtained only from the fed-batch cell culture. This increases the freshness, stability and quality of the protein, in contrast to protein obtained from both perfusion and fed-batch cultures subjected to longer periods of culture, which is thus more susceptible to degradation and generally of poorer quality. Notwithstanding, the present invention also contemplates harvesting protein from both the perfusion and fed-batch cultures (e.g., when the cells are cultured in a single bioreactor).

In certain embodiments, the present invention employs recombinant cells which express a protein of interest. For example, cells are transfected with at least one nucleic acid that encodes a protein of interest.

The methods of the present invention can be used to enhance production of any protein of interest, including, without limitation, enzymes, receptors, fusion proteins, cytokines, regulatory factors, hormones, diagnostic proteins, therapeutic proteins, and antigen-binding agents. In a particular embodiment, the protein is an antibody (or antigen binding fragment thereof). Similarly, a wide variety of cells can be cultured according to the methods of the present invention. In a particular embodiment, the cells are animal cells. In a preferred embodiment, the cells are mammalian cells, such as CHO, NSO, BHK and Per C6 cells.

The conditions of the cell culture (e.g., pH, temperature, media, particular vessel for growing the cultures, etc.) can be determined and adjusted by one of ordinary skill in the art depending on a number of factors, such as the particular cell line and protein to be produced. In one embodiment, the perfusion cell culture and fed-batch mode cell culture are performed in bioreactors. This can include a single bioreactor or multiple bioreactors (e.g., such that the perfusion cell culture and fed-batch mode cell culture are performed in separate bioreactors). For example, the perfusion cell culture can be performed in one bioreactor and then the cells can be transferred into multiple fed-batch bioreactors.

Additionally, the cell culture conditions can be optimized to maximize protein production. For example, cell culture parameters, such as pH, DO, temperature, feed strategies, feed composition, etc. can be optimized.

In other embodiments, the present invention provides methods for clarifying a protein from a cell culture. This is achieved by adjusting the pH of the cell culture to below neutral pH (i.e., below a pH of 7) and settling the cell culture, such that the cell culture separates to form a supernatant layer and a cell-bed layer, wherein the protein is present in (and can be isolated from) the supernatant layer. While the methods can be applied to cell cultures of the invention, they can be applied to clarify a protein from any cell culture, including high density cell cultures.

In one embodiment, the method involves adjusting the pH of the cell culture to a low pH (i.e., below a neutral pH of 7 such as pH of 4-7). In a particular embodiment, the pH is adjusted to a pH between about 4.5 and 6.5. In other embodiment, the method involves settling the cell culture for at least about 30 minutes, so as to enhance clarification of the cell culture in advance of collecting the protein. However, the cell culture can be settled for longer periods of time at the discretion of the skilled artisan. In a particular embodiment, the cell culture is settled for between about 30 and 120 minutes.

Other known purification techniques can optionally be employed in conjunction with the clarification method described above. For example, in one embodiment, the cell culture can be centrifuged before settling the cell culture. In another embodiment, the cell culture can be centrifuged after settling the cell culture. In yet another embodiment, the cell culture can be centrifuged before and after settling the cell culture.

Another optional step that can be taken to enhance the clarification method is washing the cell-bed layer that forms as a result of the settling process with a low pH buffer. In a particular embodiment, the pH of the buffer is the same as the pH of the cell culture, i.e., when the cell culture is adjusted to a low pH (i.e., below a neutral pH of 7).

Additionally, filtration techniques can be used to further clarify the cell culture. For example, the cell culture can be filtered before the cell culture is settled. In another embodiment, the cell culture can be filtered after the cell culture is settled. In yet a further embodiment, the cell culture can be filtered before and after the cell culture is settled. Filtration can be performed using any number of techniques known in the art, including, but not limited to depth filtration and polishing filtration.

Other features and advantages of the invention will be apparent from the following detailed description, and from the claims.

DETAILED DESCRIPTION OF THE INVENTION

The present invention provides improved methods for increasing protein production in a cell culture by growing cells that produce the protein in a perfusion cell culture to a high cell density (i.e., at least above $40 \times 10^6$ cells/mL), and then switching to a fed-batch cell culture, such that the cells enter a protein production phase. The invention further provides methods for clarifying cell cultures to facilitate collection of protein from the cultures.

In order that the present invention may be more readily understood, certain terms are first defined. Additional definitions are provided throughout the detailed description.

I. Definitions

The terms "cell culture" and "culture" include any combination of cells and medium. The methods of the present invention contemplate, without limitation, two general types of cell culture, i.e., perfusion cell culture and fed-batch cell culture. The principles behind these types of cell culture are described below.

As used herein, the terms "perfuse", "perfusion" and "perfusion culture" are used interchangeably to refer to a method of culturing cells, wherein additional fresh medium is provided to the culture and spent medium is removed from the culture. Perfusion is initiated after the culture is seeded and can occur either continuously or intermittently, as desired, over a period of time. The fresh medium added during perfusion typically provides nutritional supplements for the cells that have been depleted during the culturing process. Perfusion also allows for removal of cellular waste products and toxic byproducts from the cell culture. Perfusion is performed during the growth phase of the cells, but can also be continued after the cells have been transferred to a fed-batch cell culture (discussed below).

As used herein, the term "specific perfusion rate" (SPR) refers to the rate at which fresh medium is provided to the cell culture and spent medium is removed based on cell density. SPR can be calculated using the following equation:

$$\text{Specific Perfusion Rate (SPR)} = \text{(Reactor Volume/day)}/\text{(Total Cell Density } (\times 10^6))\text{.}$$

The SPR can be determined and/or adjusted by one of ordinary skill in the art, based on factors including, but not limited to the nature of the particular host cells, the cell growth rate, and the cell density. For example, the typical SPR can range from about 0.01 to about $1.0 \times 10^{-6}$ mL cell$^{-1}$ day$^{-1}$. In one embodiment, the SPR is 1.0, 0.9, 0.8, 0.7, 0.6, 0.5, 0.4, 0.3, 0.2, 0.1, 0.09, 0.08, 0.07, 0.06, 0.05, 0.04, 0.03, 0.02 or 0.01. In one embodiment, the SPR ranges from 0.25 to 0.03×$10^{-6}$ mL cell$^{-1}$ day$^{-1}$. In another embodiment, the SPR ranges from 0.07 to 0.01×$10^{-6}$ mL cell$^{-1}$ day$^{-}$. In another embodiment, the SPR ranges from 0.07 to 0.03×$10^{-6}$ mL cell$^{-1}$ day$^{-}$. In a particular embodiment, the SPR is maintained at about 0.05×$10^{-6}$ mL cell$^{-1}$ day$^{-1}$.

The SPR can remain constant over a period of time or it can be altered (i.e., increased or decreased) over the course of the period of perfusion. For example, the SPR can be steadily increased over time, increased in a step-wise fashion over time, steadily decreased over time, decreased in a step-wise fashion over time, or any combination thereof. The perfusion can be applied in a continuous manner or in an intermittent manner. One of ordinary skill in the art can determine the SPR, as well as the appropriate timing of the initiation and cessation of the perfusion period(s), and of any alterations to the perfusion, based upon the monitoring of some parameter of the cell culture.

As used herein, the term "fed-batch culture" refers to a method of culturing cells, wherein the cell culture is supplemented with fresh medium, i.e., the cells are "fed" with new medium while spent medium is not removed. Typically, a "fed-batch" culture process is performed in a bioreactor and additional components (e.g., nutritional supplements) are added to the culture at some time after initiation of the culture process. The controlled addition of nutrients directly affects the growth rate of the culture and allows for avoidance of the build-up of overflow metabolites (see, for example, Wlaschin, K. F. et al., "Fedbatch culture and dynamic nutrient feeding," *Cell Culture Engineering*, 101:43-74 (2006) and Lee, J. et al., "Control of fed-batch fermentations," *Biotechnol. Adv.*, 17:29-48 (1999)). A fed-batch culture is typically terminated at some point and the cells and/or components in the medium are harvested and optionally purified.

As used herein, the term "feed percentage" is the percentage of feed volume in the total volume of cell culture.

As used herein, the term "bolus feed" refers to one time feed addition

As used herein, the terms "inoculation", "inoculum", and "seeding" refer to the addition of cells to starting medium to begin the culture.

As used herein, the term "cell density" refers to the number of cells in a given volume of medium. A high cell density is desirable in that it can lead to higher protein productivity. As such, cell density is routinely monitored in cell cultures. Cell density can be monitored by any technique known in the art, including, but not limited to, extracting samples from a culture and analyzing the cells under a microscope, using a commercially available cell counting device or by using a commercially available suitable probe introduced into the bioreactor itself (or into a loop through which the medium and suspended cells are passed and then returned to the bioreactor).

As used herein the terms "super high cell density" and "high cell density" are used interchangeably and refer to a cell density of at least above 40×$10^6$ cells/mL. Known cell culture techniques may involve growing cells to a "first critical level" (i.e., "a point during the cell cycle growth phase when the cell viability may be affected by the increased concentration of waste productions (e.g., cell growth inhibitors and toxic metabolites, e.g., lactate, ammonium, etc.)" before perfusing the cell culture and obtaining roughly 5 to 40 million cells/mL). In contrast, cells grown according to the methods of the present invention are not restricted by waste products and, thus, are able to reach a super high cell density (i.e., at least above about 40, 50, 60, 70, 80, 90, 100, 110, 120, 130×$10^6$ cells/mL). Specifically, as part of the present invention it was discovered that when cells are initially grown in a perfusion cell culture, the cells grow to a much higher cell density (i.e., super high cell density), independent of the presence of waste products, such as lactate or ammonium.

In the present invention, cells grown in perfusion cell culture are "switched" (e.g., shifted or transferred) to a fed-batch culture mode once the cells reach high cell density. In one embodiment, the switch occurs at a high cell density of at least above about 40×$10^6$ cells/mL. In another embodiment, the switch occurs at a high cell density of at least between about 40×$10^6$ cells/mL and 200×$10^6$ cells/mL. In particular embodiments, the switch occurs at high cell densities of about 41×$10^6$ cells/mL, 42×$10^6$ cells/mL, 43×$10^6$ cells/mL, 44×$10^6$ cells/mL, 45×$10^6$ cells/mL, 46×$10^6$ cells/mL, 47×$10^6$ cells/mL, 48×$10^6$ cells/mL, 49×$10^6$ cells/mL, 50×$10^6$ cells/mL, 51×$10^6$ cells/mL, 52×$10^6$ cells/mL, 53×$10^6$ cells/mL, 54×$10^6$ cells/mL, 55×$10^6$ cells/mL, 56×$10^6$ cells/mL, 57×$10^6$ cells/mL, 58×$10^6$ cells/mL, 59×$10^6$ cells/mL, 60×$10^6$ cells/mL, 61×$10^6$ cells/mL, 62×$10^6$ cells/mL, 63×$10^6$ cells/mL, 64×$10^6$ cells/mL, 65×$10^6$ cells/mL, 66×$10^6$ cells/mL, 67×$10^6$ cells/mL, 68×$10^6$ cells/mL, 69×$10^6$ cells/mL, 70×$10^6$ cells/mL, 71×$10^6$ cells/mL, 72×$10^6$ cells/mL, 73×$10^6$ cells/mL, 74×$10^6$ cells/mL, 75×$10^6$ cells/mL, 76×$10^6$ cells/mL, 77×$10^6$ cells/mL, 78×$10^6$ cells/mL, 79×$10^6$ cells/mL, 80×$10^6$ cells/mL, 81×$10^6$ cells/mL m 82×$10^6$ cells/mL, 83×$10^6$ cells/mL, 84×$10^6$ cells/mL, 85×$10^6$ cells/mL, 86×$10^6$ cells/mL, 87×$10^6$ cells/mL, 88×$10^6$ cells/mL, 89×$10^6$ cells/mL, 90×$10^6$ cells/mL, 91×$10^6$ cells/mL, 92×$10^6$ cells/mL, 93×$10^6$ cells/mL, 94×$10^6$ cells/mL, 95×$10^6$ cells/mL, 96×$10^6$ cells/mL, 97×$10^6$ cells/mL, 98×$10^6$ cells/mL, 99×$10^6$ cells/mL, 100×$10^6$ cells/mL, 101×$10^6$ cells/mL, 102×$10^6$ cells/mL, 103×$10^6$ cells/mL, 104×$10^6$ cells/mL, 105×$10^6$ cells/mL, 106×$10^6$ cells/mL, 107×$10^6$ cells/mL, 108×$10^6$ cells/mL, 109×$10^6$ cells/mL, 110×$10^6$ cells/mL, 111×$10^6$ cells/mL, 112×$10^6$ cells/mL, 113×$10^6$ cells/mL, 114×$10^6$ cells/mL, 115×$10^6$ cells/mL, 116×$10^6$ cells/mL, 117×$10^6$ cells/mL, 118×$10^6$ cells/mL, 119×$10^6$ cells/mL, 120×$10^6$ cells/mL, 121×$10^6$ cells/mL, 122×$10^6$ cells/mL, 123×$10^6$ cells/mL, 124×$10^6$ cells/mL, 125×$10^6$ cells/mL, 126×$10^6$ cells/mL, 127×$10^6$ cells/mL, 128×$10^6$ cells/mL, 129×$10^6$ cells/mL, 130×$10^6$ cells/mL, 131×$10^6$ cells/mL, 132×$10^6$ cells/mL, 133×$10^6$ cells/mL, 134×$10^6$ cells/mL, 135×$10^6$ cells/mL, 136×$10^6$ cells/mL, 137×$10^6$ cells/mL, 138×$10^6$ cells/mL, 139×$10^6$ cells/mL, 140×$10^6$ cells/mL, 141×$10^6$ cells/mL, 142×$10^6$ cells/mL, 143×$10^6$ cells/mL, 144×$10^6$ cells/mL, 145×$10^6$ cells/mL, 146×$10^6$ cells/mL, 147×$10^6$ cells/mL, 148×$10^6$ cells/mL, 149×$10^6$ cells/mL, 150×$10^6$ cells/mL, 151×$10^6$ cells/mL, 152×$10^6$ cells/mL, 153×$10^6$ cells/mL, 154×$10^6$ cells/mL, 155×$10^6$ cells/mL, 156×$10^6$ cells/mL, 157×$10^6$ cells/mL, 158×$10^6$ cells/mL, 159×$10^6$ cells/mL, 160×$10^6$ cells/mL, 161×$10^6$ cells/mL, 162×$10^6$ cells/mL, 163×$10^6$ cells/mL, 164×$10^6$ cells/mL, 165×$10^6$ cells/mL, 166×$10^6$ cells/mL, 167×$10^6$ cells/mL, 168×$10^6$ cells/mL, 169×$10^6$ cells/mL, 170×$10^6$ cells/mL, 171×$10^6$ cells/mL, 172×$10^6$ cells/mL, 173×$10^6$ cells/mL, 174×$10^6$ cells/mL, 175×$10^6$ cells/mL, 176×$10^6$ cells/mL, 177×$10^6$ cells/mL, 178×$10^6$ cells/mL, 179×$10^6$ cells/mL, 180×$10^6$ cells/mL, 181×$10^6$ cells/mL, 182×$10^6$ cells/mL, 183×$10^6$ cells/mL, 184×$10^6$ cells/mL, 185×$10^6$ cells/mL, 186×$10^6$ cells/mL, 187×$10^6$ cells/mL, 188×$10^6$ cells/mL, 189×$10^6$ cells/mL, 190×$10^6$ cells/mL, 191×$10^6$ cells/mL, 192×$10^6$ cells/mL, 193×$10^6$ cells/mL, 194×$10^6$ cells/mL, 195×$10^6$ cells/mL, 196×$10^6$ cells/mL, 197×$10^6$ cells/mL, 198×$10^6$ cells/mL, 199×$10^6$ cells/mL or 200×$10^6$ cells/mL, or more. In a preferred embodiment, the switch from perfusion culture to fed-batch culture occurs at a cell density of at least about 50×10⁶ cells/mL. In a more preferred embodiment, the switch occurs at a cell density of at least about 100×10⁶ cells/mL.

As used herein, the term "super density fed-batch process," "SDF process", and "super density fed-batch cell culture process" are used interchangeably and refer to the process of growing cells in a perfusion cell culture and then transferring the cells to a fed-batch culture mode, once the cells reach high cell density (e.g., at least above 40×10⁶ cells/mL).

The transition from perfusion cell culture to fed-batch cell culture occurs once a high cell density is achieved (as discussed above). A high cell density may be achieved at any time after inoculation of the cell culture, depending on the growth rate of the cell line and the seeding density. In one embodiment, the high density may be reached 2, 3, 4, 5, 6, 7, 8, 9, 10, 11, 12, 13, 14, 15, 16, 17, 18, 19, 20, 21, 23, 24 or 25 days post-inoculation. In a preferred embodiment, the high density is reached between about 4 to 17 days post-inoculation.

As used herein, the term "viable cell density" refers to the number of live cells present in a given volume of medium under a given set of experimental conditions.

As used herein, the term "cell viability" refers to the ability of cells in culture to survive under a given set of conditions or experimental variations. The term as used herein also refers to that portion of cells that are alive at a particular time in relation to the total number of cells (e.g., living and dead) in the culture at that time.

As used herein, "the growth phase" of a cell culture refers to the phase during which the viable cell density at any time point is higher than at any previous time point.

As used herein, the "production phase" of a cell culture refers to the phase during which the cells produce significant amounts of protein, which accumulates for future processing.

As used herein, the term "cell integral" refers to the overall viable cell numbers during the course of a cell growth profile.

As used herein, the term "titer" refers to the total amount of protein produced by a cell culture, divided by a given amount of medium volume. In essence, the term "titer" refers to a concentration and is typically expressed in units of milligrams of polypeptide per liter of medium. The methods of the present invention have the effect of substantially increasing polypeptide product titer, as compared to polypeptide product titer produced from other cell culture methods known in the art.

As used herein, the terms "media", "cell culture media" and "culture media", including grammatical variations thereof, are used interchangeably, and refer to the nutrient solution in which cells (preferably animal or mammalian cells) are grown in culture. Cell culture media is the physio-chemical, nutritional, and hormonal environment for cells and typically includes at least one or more components from the following: an energy source (e.g., in the form of a carbohydrate such as glucose); essential amino acids, including the twenty basic amino acids plus cysteine; vitamins and/or other organic compounds typically required at low concentrations; lipids or free fatty acids (e.g., linoleic acid); and trace elements (e.g., inorganic compounds or naturally occurring elements that are typically required at very low concentrations, usually in the micromolar range). Media may be solid, gelatinous, liquid, gaseous or a mixture of phases and materials.

The cells utilized in the methods of the present invention can be grown and maintained in any number of cell culture media which are known in the art or are commercially available. One of ordinary skill in the art may opt to use one or more known cell culture media that is selected to maximize cell growth, cell viability, and/or protein production in a particular cultured host cell. Exemplary cell culture media include any media suitable for culturing cells that can express a protein of interest, including, but not limited to animal component free medium, such as EX-CELL® TiterHigh medium (SAFC), and chemically defined media, such as CD CHO medium (Invitrogen, Carlsbad, Calif.) and CD Opti-CHO (Invitrogen, Carlsbad, Calif.))

Additionally, the cell culture media can optionally be supplemented to include one or more additional components, in appropriate concentrations or amounts, as necessary or desired, and as would be known and practiced by those of ordinary skill in the art. Exemplary supplements include, but not limited to, chemical gene selection agents, hormones and other growth factors, (e.g., insulin, transferrin, epidermal growth factor, serum, somatotropin, pituitary extract, aprotinin); salts (e.g., calcium, magnesium and phosphate), and buffers (e.g., HEPES (4-[2-Hydroxethyl]-1-piperazine-ethanesulfonic acid)); nucleosides and bases (e.g., adenosine, thymidine, hypoxanthine); protein and hydrolysates; antibiotics (e.g., gentamycin); cell protective agents (e.g., a Pluronic polyol (PLURONIC® F68)) and extracellular matrix proteins (e.g., fibronectin). Supplements that support the growth and maintenance of particular cell cultures are able to be readily determined by those of ordinary skill in the art, such as is described, for example, by Barnes et al. (*Cell*, 22:649 (1980)); in *Mammalian Cell Culture*, Mather, J. P., ed., Plenum Press, NY (1984); and in U.S. Pat. No. 5,721,121.

As used herein, the term "bioreactor" refers to any apparatus, closed container or vessel (e.g., a fermentation chamber) that is used for growing cell cultures. Bioreactors allow controlling various parameters during the cell culture process including, but not limited to, the circulation loop flow, pH, the temperature, the overpressure and/or the medium perfusion rate. Bioreactors include commercially available bioreactors, classical fermenters and cell culture perfusion systems, as well as disposable bioreactors.

The bioreactor can be of any size that is useful for culturing cells at a desirable scale in accordance with a method of the invention. For example, a bioreactor employed in the methods of the present invention may be at least 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 340, 350, 360, 370, 380, 390, 400, 410, 420, 430, 440, 450, 460, 470, 480, 490, 500, 550, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,0000, 13,000, 14,000, 15,000 liters or more, or any intermediate volume.

The methods of the present invention can employ one or more bioreactors. For example, in one embodiment, the perfusion cell culture and fed-batch cell culture can be performed in the same bioreactor. In another embodiment, the perfusion cell culture can be performed in separate bioreactors. In another embodiment, the cells from the perfusion cell culture can be transferred to multiple fed-batch bioreactors.

A suitable bioreactor may be composed of (i.e., constructed of) any material that is suitable for holding cell cultures under the culture conditions of the present invention and is conducive to cell growth and viability. For example, a bioreactor employed in the methods of the present invention can be made of glass, plastic or metal. However, the materials comprising the bioreactor should not interfere with expression or stability of the polypeptide product. Suitable bioreactors are known in the art and commercially available.

A perfusion bioreactor used in the methods of the present invention can be a disposable perfusion bioreactor or any other traditional perfusion bioreactors. The bioreactor may optionally be equipped with any internal or external cell retention devices, including, but not limited to, spin filters, tangential flow membrane filters, dynamic membranes, ultrasonic separators, gravity settlers, continuous centrifuge or acoustic cell retention device, microfiltration devices, ultrafiltration devices, etc. In a particular embodiment, the bioreactor is a disposable bioreactor equipped with microfiltration membrane having a pore size of 1.2 to 10 µm.

As used herein, the term "antifoam" refers to an agent that can be added to a cell culture to prevent the build up of excess foam. Examples of antifoam agents include, but are not limited to, 3% simethicone manufactured by Invitrogen and HyClone. Antifoams are commercially available and can be used at the discretion of one of ordinary skill in the art.

The cell cultures encompassed by the methods of the present invention may be grown at any temperature appropriate for the cell type and culture conditions. In one embodiment, it is desirable to use a temperature between about 30° C. and 38° C., to enhance protein production. In another embodiment, the temperature is at least about 25° C., 26° C., 27°, 28° C., 29° C., 30° C., 31° C., 32° C., 33° C., 34° C., 35° C., 36° C., 37° C., 38° C., 39° C., 40° C., or 41° C. It may also be desirable to use different temperatures at different times during the culture.

A. Cell Culture

As used herein, the term "cell", refers to animal cells, mammalian cells, cultured cells, host cells, recombinant cells, and recombinant host cells. Such cells are generally cell lines obtained or derived from mammalian tissues which are able to grow and survive when placed in media containing appropriate nutrients and/or growth factors. The cells utilized in the methods of the present invention are generally animal or mammalian cells that can express and secrete, or that can be molecularly engineered to express and secrete, large quantities of a particular protein into the culture medium. In one embodiment, the protein produced by the cell can be endogenous or homologous to the cell. Alternatively, the protein is heterologous, i.e., foreign, to the cell.

Any eukaryotic cell that is capable of expressing the protein of interest can be cultured according to the methods of the present invention. Numerous cell lines are available from commercial sources, including, but not limited to the American Type Culture Collection (ATCC). In one embodiment of the invention, the cell culture employs hybridoma cells. The construction of antibody-producing hybridoma cells is well known in the art. In another embodiment of the invention, the cell culture employs CHO cells.

Representative cells that can be used in the methods of the present invention include, but are not limited to, Chinese hamster ovary cells (CHO), NS0, Per C6, HEK, COS, VERO076, BRL-3A, HepG2, MRC 5, 293T, A431, 3T3, CV-1, C3H10T1/2, Colo205, 293, L cells, HL-60, FRhL-2, U937, HaK, Jurkat cells, Rat2, BaF3, 32D, FDCP-1, PC12, Mix, murine myelomas (e.g., SP2/0 and NS0) and C2C12 cells, DG44 (Chasin et al., *Som. Cell Molec. Genet.*, 12:555-556 (1986); and Kolkekar et al., *Biochemistry*, 36:10901-10909 (1997)), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub et al., *Proc. Natl. Acad. Sci. USA*, 77:4216 (1980)), and dp12.CHO cells (U.S. Pat. No. 5,721,121); monkey kidney CV1 cells transformed by SV40 (COS cells, COS-7, ATCC® CRL-1651); human embryonic kidney cells (e.g., 293 cells, or 293 cells subcloned for growth in suspension culture, Graham et al., *J. Gen. Virol.*, 36:59 (1977)); baby hamster kidney cells (BHK, ATCC® CCL-10); monkey kidney cells (CV1, ATCC® CCL-70); African green monkey kidney cells (VERO-76, ATCC® CRL-1587; VERO, ATCC® CCL-81); mouse sertoli cells (TM4, Mather, *Biol. Reprod.*, 23:243-251 (1980)); human cervical carcinoma cells (HELA, ATCC® CCL-2); canine kidney cells (MDCK, ATCC® CCL-34); human lung cells (W138, ATCC® CCL-75); human hepatoma cells (HEP-G2, HB 8065); mouse mammary tumor cells (MMT 060562, ATCC® CCL-51); buffalo rat liver cells (BRL 3A, ATCC® CRL-1442); TRI cells (Mather, *Annals NY Acad. Sci.*, 383:44-68 (1982)); MCR 5 cells; FS4 cells, as well as transformed primate cell lines, hybridomas, normal diploid cells, and cell strains derived from in vitro culture of primary tissue and primary explants.

Cells suitable for culturing in the methods of the present invention can contain introduced (e.g., via transformation, transfection, infection, or injection) expression vectors (constructs), such as plasmids and the like, that harbor coding sequences (or portions thereof), which encode a desired protein. Such expression vectors contain the necessary elements for the transcription and translation of the inserted coding sequence and generally include, but are not limited to, one or more of the following: a signal sequence, one or more marker genes, an enhancer element, a promoter, and a transcription termination sequence.

Methods and techniques to construct expression vectors containing sequences encoding the produced proteins, as well as the appropriate transcriptional and translational control elements, are well known in the art. Such methods include in vitro recombinant DNA techniques, synthetic techniques, and in vivo genetic recombination (see, for example, Sambrook J. et al., *Molecular Cloning, A Laboratory Manual*, Cold Spring Harbor Press, Plainview, N.Y. (1989) and in Ausubel, F. M. et al., *Current Protocols in Molecular Biology*, John Wiley & Sons, New York, N.Y. (1989)).

Expression constructs can be introduced into cells by a wide variety of routine gene transfer methods known in the art. For example, such methods can include, but are not limited to, conventional gene transfection methods, such as calcium phosphate co-precipitation, liposomal transfection, microinjection, electroporation, and infection or viral transduction (see, for example, U.S. Pat. No. 4,399,216, Keown et al., *Methods in Enzymology* (1989), Keown et al., *Methods in Enzymology*, 185:527-537 (1990), and Mansour et al., *Nature*, 336:348-352 (1988).

Any number of known expression vectors can be suitable for eukaryotic host cells cultured according to the methods of the invention, including, but not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc vectors, pCMV vectors, pSG5 vectors (Stratagene), retroviral vectors (e.g., pFB vectors (Stratagene)), pcDNA-3 (Invitrogen), adenoviral vectors; Adeno-associated virus vectors, baculovirus vectors, yeast vectors (e.g., pESC vectors (Stratagene)), or modified forms of any of the foregoing. Vectors can also contain enhancer sequences upstream or downstream of promoter region sequences for optimizing gene expression.

Control elements (e.g., regulatory sequences), are those non-translated regions of the vector, e.g., enhancers, promoters, 5' and 3' untranslated regions, that interact with host cellular proteins to carry out transcription and translation.

Such elements vary in their strength and specificity. Depending on the vector system and particular host cell, any number of suitable transcription and translation elements, including constitutive and inducible promoters, can be used. In mammalian cell systems, promoters from mammalian genes or from mammalian viruses are preferred. The constructs for use in protein expression systems are designed to contain at least one promoter, an enhancer sequence (optional, for mammalian expression systems), and other sequences as necessary or required for proper transcription and regulation of gene expression (e.g., transcriptional initiation and termination sequences, origin of replication sites, polyadenylation sequences). The selection of an appropriate vector for proper transcription, expression, and isolation of proteins produced in eukaryotic (e.g., mammalian) expression systems is known and well within the ordinary skill in the art.

Commonly used eukaryotic control sequences for use in mammalian expression vectors include promoters and control sequences compatible with mammalian cells, such as, for example, the cytomegalovirus (CMV) promoter (CDM8 vector) and avian sarcoma virus (ASV). Other commonly used promoters include the early and late promoters from Simian Virus 40 (SV40) (Fiers et al., *Nature*, 273:113 (1973)), or other viral promoters such as those derived from polyoma, Adenovirus 2, and bovine papilloma virus. An inducible promoter, such as hMTII (Karin et al., *Nature*, 299:797-802 (1982)) can also be used.

B. Protein Production

As used herein, the terms "polypeptide", "polypeptide product", "protein" and "protein product," are used interchangeably and, as is known in the art, refer to a molecule consisting of two or more amino acids, e.g., at least one chain of amino acids linked via sequential peptide bonds. In one embodiment, a "protein of interest" or a "polypeptide of interest" is a protein encoded by an exogenous nucleic acid molecule that has been transformed into a host cell, wherein the exogenous DNA determines the sequence of amino acids. In another embodiment, a "protein of interest" is a protein encoded by a nucleic acid molecule that is endogenous to the host cell.

Numerous polypeptides can be produced by the methods of the present invention. Exemplary polypeptides include gene products, naturally-occurring proteins, homologs, orthologs, paralogs, fragments, and other equivalents, variants and analogs of the foregoing. Polypeptides may also include one or more modifications such as, for example, a lipid moiety, a phosphate, a sugar moiety, etc. Particular polypeptides that may be desirable for expression in a method of the invention include, but are not limited to, cytokines, cytokine receptors, growth factors (e.g., epidermal growth factor (EGF), human epidermal growth factor receptor-2 (HER-2), fibroblast growth factor-alpha (FGF-α), fibroblast growth factor-beta (FGF-β), transforming growth factor-alpha (TGF-α), transforming growth factor-beta (TGF-β), platelet-derived growth factor (PDGF), insulin-like growth factor-1 (IGF-1), insulin-like growth factor-2 (IGF-2), nerve growth factor (NGF), nerve growth factor-beta (NGF-β)); growth factor receptors, including fusion or chimeric proteins, growth hormones (e.g., human growth hormone, bovine growth hormone); insulin (e.g., insulin A chain and insulin B chain), proinsulin; erythropoietin (EPO); colony stimulating factors (e.g., granulocyte colony-stimulating factor (G-CSF), granulocyte macrophage colony-stimulating factor (GM-CSF), macrophage colony-stimulating factor (M-CSF)); interleukins (e.g., IL-1 through IL-12); vascular endothelial growth factor (VEGF) and its receptor (VEGF-R); interferons (e.g., IFN-α, β, or γ) and their receptors; tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor LX, von Willebrands factor, and the like); anti-clotting factors; tissue plasminogen activator (TPA), e.g., urokinase or human urine or tissue type TPA; follicle stimulating hormone (FSH); luteinizing hormone (LH); calcitonin; CD proteins (e.g., CD3, CD4, CD8, CD28, CD 19, etc.); CTLA proteins (e.g., CTLA4); T-cell and B-cell receptor proteins; bone morphogenic proteins (BMPs, e.g., BMP-1, BMP-2, BMP-3, etc.); neurotrophic factors, e.g., bone derived neurotrophic factor (BDNF); neurotrophins, e.g., 3-6; renin; rheumatoid factor; RANTES (regulated on activation normally T-cell expressed and secreted); albumin; relaxin; relaxin A-chain; relaxin B-chain; prorelaxin; macrophage inhibitory protein (e.g., MIP-1, MIP-2); viral proteins or antigens; surface membrane proteins; ion channel proteins; enzymes; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-β), parathyroid hormone; thyroid stimulating hormone; lipoproteins; glucagon; atrial natriuretic factor; lung surfactant; bombesin; hemopoietic growth factor; enkephalinase; a serum albumin (e.g., human serum albumin); mullerian-inhibiting substance; gonadotropin-associated peptide; DNase; inhibin; activin; receptors for hormones or growth factors; integrin; protein A or D; CD proteins such as CD-3, CD-4, CD-8, and CD-19; PD-1 and PD-L1 (B7-H1 and ligand); and B7-H4, osteoinductive factors; immunotoxins; decay accelerating factor; and others as known in the art, fusion proteins and polypeptides, chimeric proteins and polypeptides, and fragments or portions, or mutants, variants, or analogues of any of the aforementioned proteins and polypeptides.

In further embodiments, methods of the present invention can be used to produce immunoglobulins (e.g., antibodies), immunoglobulin-like domain-containing molecules (e.g., ankyrin or fibronectin domain-containing molecules), and Fc-fusion proteins. The term "Fc-fusion protein", as used herein, is meant to encompass therapeutic proteins comprising an immunoglobulin-derived moiety (i.e., an Fc moiety) and a moiety derived from a second, non-immunoglobulin protein.

In a particular embodiment of the invention, the polypeptide produced by the methods of the present invention is an antibody. The term "antibody" is used in the broadest sense to cover any type of known antibody, including, but is not limited to, monoclonal antibodies (including full length monoclonal antibodies), polyclonal antibodies, monospecific antibodies, multispecific antibodies (e.g., bispecific antibodies), immunoadhesins, antibody-immunoadhesin chimeras, humanized, human, chimeric, single-chain, synthetic, recombinant, hybrid, mutated, grafted, or in vitro generated antibodies. The antibody can be a full length antibody or an antibody fragment. The antibody may be selected from any of the known antibody isotypes, for example, IgA, IgG, IgD, IgE, IgM. The antibody may be a monomer, dimer, or multimer (e.g., a trimer or pentamer).

The term "antibody" or "immunoglobulin," as used interchangeably herein, includes whole antibodies and any antigen binding fragment (i.e., "antigen-binding portion") or single chains thereof. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al., Nature, 341:544-546 (1989)), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc. Natl. Acad. Sci. USA, 85:5879-5883 (1988)). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. For example, monoclonal antibodies can be produced using conventional hybridoma technology first described by Kohler et al., Nature, 256:495 (1975), or they can be made using recombinant DNA methods (see, e.g., U.S. Pat. No. 4,816,567).

Monoclonal antibodies can also be isolated from phage antibody libraries, e.g., using the techniques described in Clackson et al., Nature, 352:624-628 (1991); Marks et al., J. Mol. Biol., 222:581-597 (1991); and U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915; and 6,593,081.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai et al., Clin. Exp. Immunol., 79:315-321 (1990); Kostelny et al., J. Immunol., 148:1547-1553 (1992).

An "isolated antibody," as used herein, is intended to refer to an antibody which is substantially free of other antibodies having different antigenic specificities. In addition, an isolated antibody is typically substantially free of other cellular material and/or chemicals. In one embodiment of the invention, multiple "isolated" monoclonal antibodies having different binding specificities are combined in a well defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype.

Monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature, 321:522-525 (1986); Riechmann et al., Nature, 332:323-329 (1988); and Presta, Curr. Op. Struct. Biol., 2:593-596 (1992). Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see, e.g., U.S. Pat. No. 4,816,567 to Cabilly et al.). To create a humanized antibody, the murine CDR regions can be inserted into a human framework using methods known in the art (see, e.g., U.S. Pat. No. 5,225,539 to Winter, and U.S. Pat. Nos. 5,530,101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-MOUSE® (Medarex, Inc., Princeton, N.J.) which has a human heavy chain transgene and a human light chain transchromosome (see WO 02/43478), XENOMOUSE® (Abgenix, Inc., Fremont Calif.; described in, e.g., U.S. Pat. Nos. 5,939,598; 6,075,181; 6,114,598; 6, 150,584 and 6,162,963 to Kucherlapati et al.), and HUMAB-MOUSE® (Medarex, Inc.; described in, e.g., Taylor, L. et al., *Nucleic Acids Research,* 20:6287-6295 (1992); Chen, J. et al., *International Immunology,* 5:647-656 (1993); Tuaillon et al., *Proc. Natl. Acad. Sci. USA,* 90:3720-3724 (1993); Choi et al., *Nature Genetics,* 4:117-123 (1993); Chen, J. et al., *EMBO J.,* 12: 821-830 (1993); Tuaillon et al., *J. Immunol.,* 152:2912-2920 (1994); Taylor, L. et al., *International Immunology,* 6: 579-591 (1994); and Fishwild, D. et al., *Nature Biotechnology,* 14:845-851 (1996); U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Another example of the type of protein that may be produced using the methods of the present invention is a fusion protein. A fusion protein is a protein, or domain or a protein (e.g., a soluble extracellular domain) fused to a heterologous protein or peptide. Representative fusion proteins include, but are not limited to, proteins expressed as a fusion with a portion of an immunoglobulin molecule, proteins expressed as fusion proteins with a zipper moiety, and novel polyfunctional proteins, such as a fusion protein of a cytokine and a growth factor. WO 93/08207 and WO 96/40918 describe the preparation of various soluble oligomeric forms of a molecule referred to as CD40L, including an immunoglobulin fusion protein and a zipper fusion protein, respectively. The techniques described in WO 93/08207 and WO 96/40918 are applicable to other proteins. Generally speaking, any molecule can be expressed as a fusion protein including, but not limited to, the extracellular domain of a cellular receptor molecule, an enzyme, a hormone, a cytokine, a portion of an immunoglobulin molecule, a zipper domain, and an epitope.

C. Cell Culture Clarification and Purification

The present invention further provides improved methods for clarifying a cell culture e.g., so as to facilitate collection of the expressed protein. Specifically, the present invention provides a method for clarifying a protein from a cell culture by adjusting the pH of the cell culture to below neutral pH (i.e., below a pH of 7) and settling the cell culture, such that the cell culture separates to form a supernatant layer and a cell-bed layer, wherein the protein is present in and can be isolated from the supernatant layer. In certain embodiments, methods of the present invention comprise steps to enhance the clarification process. For example, after the protein is isolated from the supernatant layer, the methods may further comprise washing the cell-bed with the same pH buffer, additional settling, and additional filtration such that more protein yield can be obtained from the cell culture. The clarification methods described herein can be used in combination with the above-described cell culture method or any other cell culture method.

As used herein, the term "cell culture supernatant layer" refers to the liquid fraction of the cell culture, including the liquid phase of the cell-bed.

As used herein, the term "cell bed layer" refers to the biomass layer of the cell culture.

As used herein, the term "settling" refers to the process of allowing the cell culture to sit undisturbed for a period of time, so as to facilitate separation of the supernatant from the cell-bed. The cell culture can be settled for any period of time, including but not limited to about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, and 145 minutes. In one embodiment, the cell culture can be settled for between about 30-120 minutes. In another embodiment, the cell culture can be settled for between about 30-60, 60-90 or 90-120 minutes.

Cell cultures can be clarified using the methods described herein either alone or in combination with other known clarification and purification techniques. Such known processes included, but are not limited to, filtration, centrifugation, precipitation (e.g., ethanol precipitation or ammonium sulfate precipitation), phase separation, affinity purification, gel filtration, ion exchange chromatography, hydrophobic interaction chromatography (HIC; using such resins as phenyl ether, butyl ether, or propyl ether), HPLC, or fractionation on immunoaffinity or ion-exchange columns, reverse SDS-PAGE, or any combination of these techniques. A protease inhibitor such as phenyl methyl sulfonyl fluoride (PMSF) also may be useful to inhibit proteolytic degradation during clarification.

One skilled in the art will appreciate that clarification methods suitable for the protein of interest may require modification to account for changes in the character of the protein upon expression in recombinant cell culture. Additionally, the desired degree of clarification depends on the particular protein and the intended use of the protein. The proteins ultimately isolated using the methods described herein can be suitable for therapeutic and diagnostic uses.

As used herein, the term "depth filtration" refers to a type of filtration performed using a depth filter. A depth filter usually has multiple layers of filtration media, each of varying size and density, which become progressively finer and denser in the lower layer. A depth filter traps particular within it structure, not just on the surface.

As used herein, the term "polishing filtration" refers to a finer grade of depth filtration and membrane filtration.

The present invention is further illustrated by the following examples which should not be construed as further limiting.

The contents of all figures and all references, patents and published patent applications cited throughout this application are expressly incorporated herein by reference in their entireties.

EXAMPLES

Example 1

Super Density Fed-Batch Cell Culture Process

A. Experimental Methods

Recombinant CHO cells (i.e., antibody producing CHOK1SV cells) were expanded in cell culture flasks before inoculating the Wave perfusion bioreactor. The perfusion bioreactor was operated with the same basal medium that is used in cell expansion process. The perfusion rate was adjusted to maintain a healthy culture with high cell viabilities. In certain experiments, cells were concentrated to a higher cell density, as appropriate, by adjusting the medium in and out flow rates. Once the viable cell density reached greater than $50 \times 10^6$ cells/mL, fed-batch production process was started. The culture was fed by a combination of bolus and continuous feeding modes, so as to control the osmolality and glucose level. The cell culture was then harvested when cell viability decreased to approximately 60-10%.

B. Experiment 1

Figure 1:
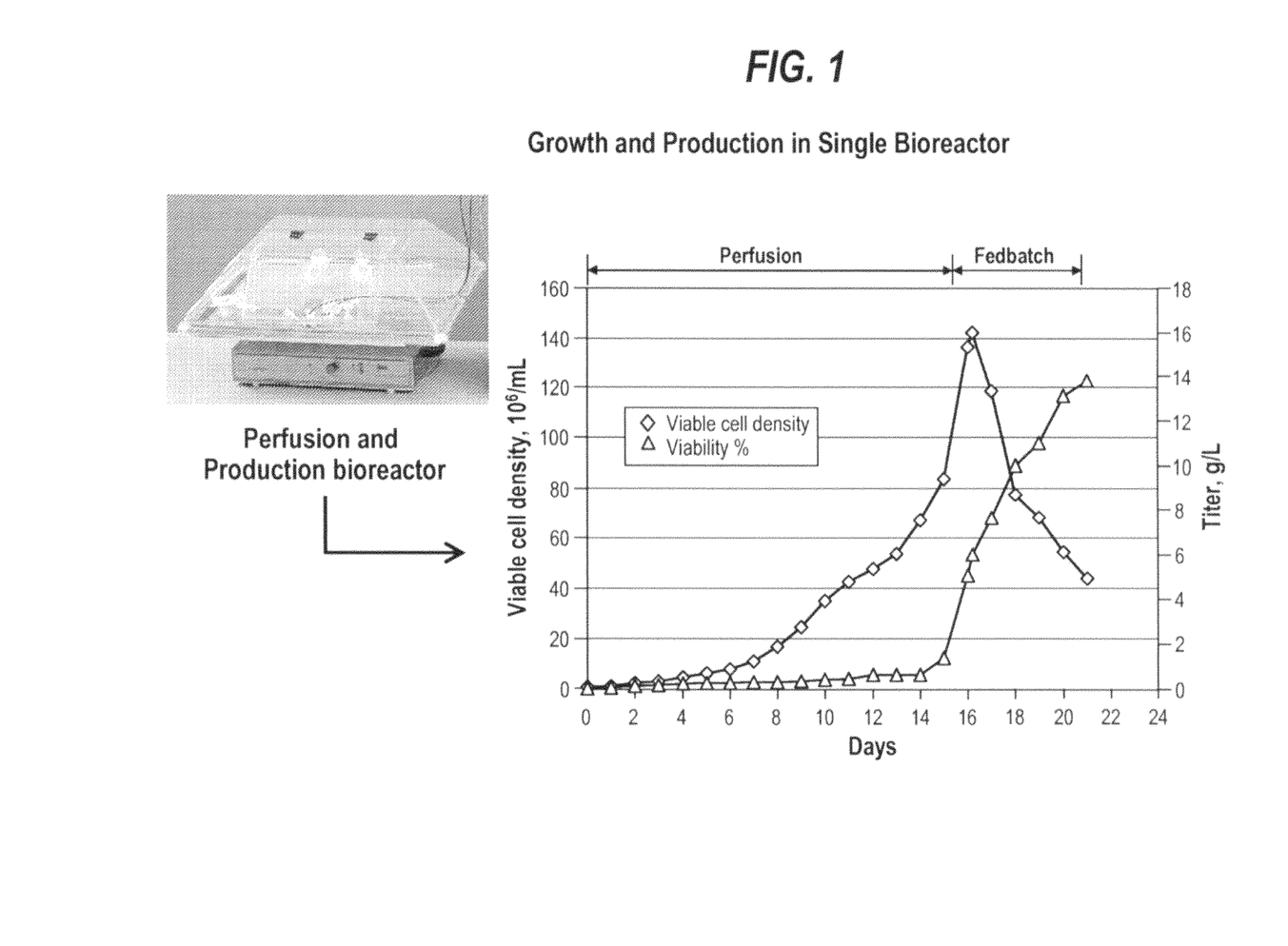
FIG. 1 depicts one possible scenario for practicing the methods of the present invention, i.e., wherein the super density fed-batch cell culture process is performed in a single bioreactor.
Figure 2:
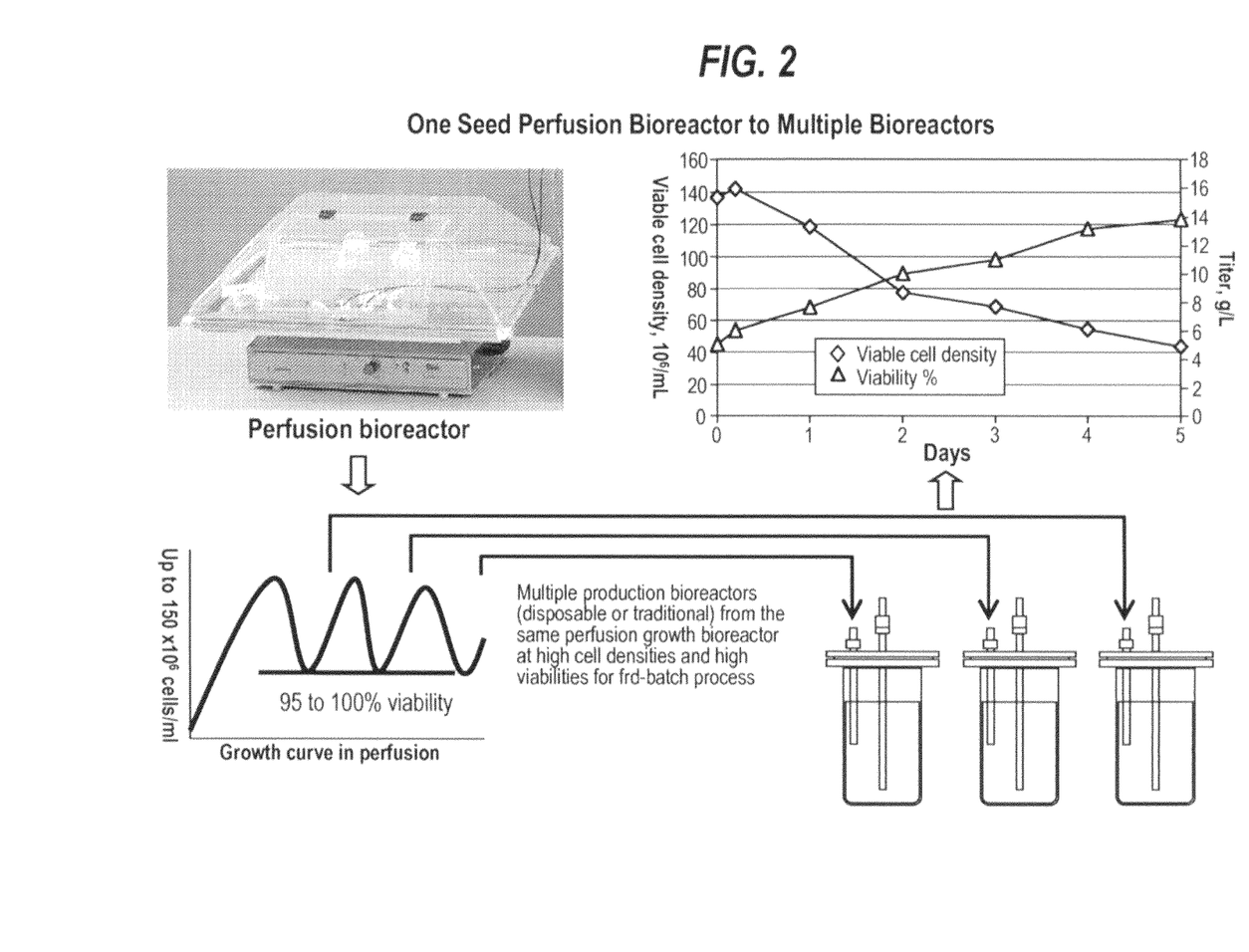
FIG. 2 depicts another possible scenario for practicing the methods of the present invention, i.e., wherein the cells are perfused in a perfusion bioreactor until a particular density of cells is achieved and then transferred to multiple fed batch reactors. Fed-batch cell culture process is performed in a single bioreactor.
Figure 3:
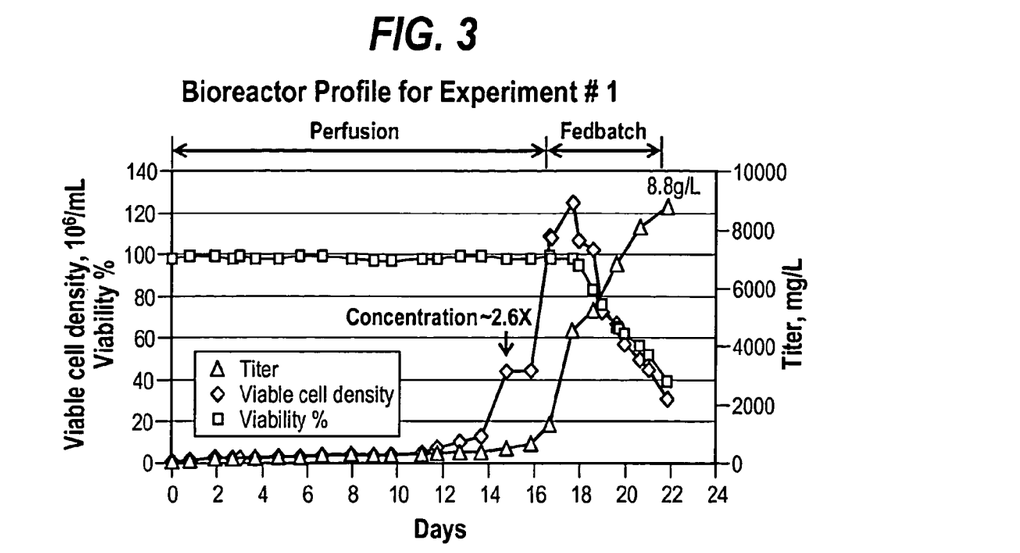
FIG. 3 is a graph showing the cell growth and protein production profile for Experiment #1.

Cells were inoculated in a BIOSTAT Cultibag (Sartorius) at approximately $0.84 \times 10^6$ cells/mL. The specific perfusion rate (SPR) ranged from 0.25 to $0.03 \times 10^{-6}$ mL cell$^{-1}$ day$^{-1}$. Cells were concentrated about 2.6 fold when viable cell density reached $12.6 \times 10^6$ cells/mL. After concentration, cells were grown up to $108.8 \times 10^6$ cells/mL. Once the cells reached $108.8 \times 10^6$ cells/mL, perfusion was stopped and the fed-batch process was started immediately. During the fed-batch process, one or two bolus feeds at 3 to 10% (i.e., percentage of feed to post feed volume) were performed every day to maintain cell viability. Glucose was also supplemented by bolus feed to maintain a sufficient level. Cell density reached $124.66 \times 10^6$ cells/mL with 98% viability the second day after fed-batch process started. The total feed percentage was about 40%. As shown in the growth and production profile depicted in FIG. 3, a final productivity of 8.8 g/L from fed-batch process was achieved after 6 days at 39% viability.

C. Experiment 2

Cells were inoculated in the WAVE BIOREACTOR® (GE Healthcare, Fairfield, Conn.) at approximately $0.81 \times 10^6$ cells/mL. The rate of specific perfusion (SPR) ranged from 0.07 to $0.01 \times 10^{-6}$ mL cell$^{-1}$ day$^{-1}$ and varied at different time points. The cells were concentrated about 1.5 fold overnight between days 15 and 16. On day 16, the cell density reached up to $136.5 \times 10^6$ cells/mL. At this point in time, the perfusion process was stopped and the fed-batch process was started. One or two bolus feeds at 1 to 6% were performed in the first two days to maintain cell viability. Continuous feeding of glucose and/or other nutrients was started on the first day of the fed-batch process to maintain glucose level, as well as to promote a favorable osmolality increasing trend, while providing sufficient nutrients.

Figure 4:
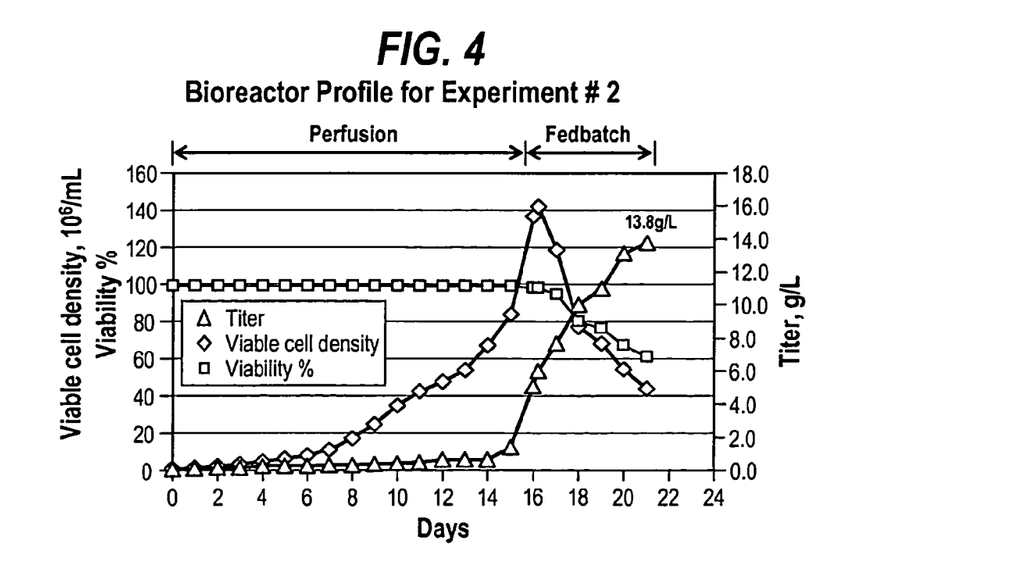
FIG. 4 is a graph showing the cell growth and protein production profile for Experiment #2.

The cells grew to $142.0 \times 10^6$ cells/mL about 7 hours after fed-batch process started and the total feed percentage was about 28%. As shown in the growth and production profile depicted in FIG. 4, a final productivity of 13.8 g/L was achieved after 6 days at 61% viability from fed-batch production phase.

During this experiment, it was noted that feed components fell out of solution in the pump tubing during the continuous feeding process, possibly due to a slow flow rate. As such, some modifications of feeds were made in a subsequent study (see Experiment #5 below) to prevent precipitation of feed components in the pump tubing.

D. Experiment 3

Figure 5:
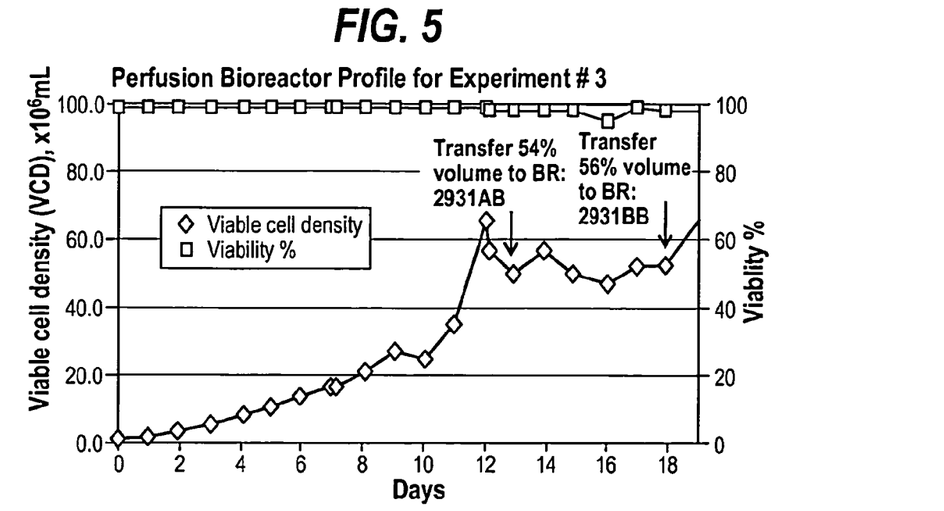
FIG. 5 is a graph depicting the perfusion bioreactor profile (i.e., viable cell density and percent viability) of Experiment 3.
Figure 6:
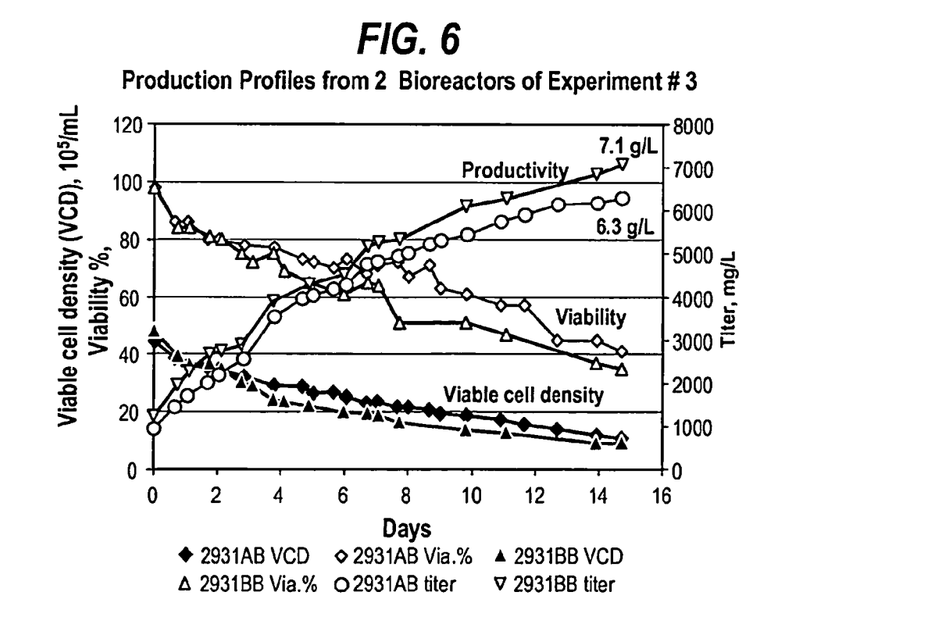
FIG. 6 is an overlay graph depicting the cell density and productivity profiles from the two bioreactors utilized in Experiment 3.

Cells were inoculated in the WAVE BIOREACTOR® (GE Healthcare, Fairfield, Conn.) at approximately $1.20 \times 10^6$ cells/mL. The rate of specific perfusion (SPR) ranged from 0.07 to 0.03 (e.g., $0.05) \times 10^{\times 6}$ mL cell$^{-1}$ day$^{-1}$ and varied at different time points. As shown in FIG. 5, cells were partially transferred on day 13 and day 18 to two separate 5 liter stir tank bioreactors at a cell density of approximately $50 \times 10^6$ cells/mL. Antifoam was also added to overcome foaming in the bioreactors. As shown in the growth and production profile depicted in FIG. 5, a final productivity of 6.3 g/L at about 40% viability was achieved from the fed-batch cells transferred on day 13 (i.e., 2391AB) (see FIG. 6). A final productivity of 7.1 g/L at about 38% viability was achieved from the fed-batch cells transferred on day 18 (i.e., 2391BB) (see FIG. 6).

E. Experiment 4

A further perfusion run was performed to repeat the cell culture process of the foregoing examples in a single perfusion bioreactor (i.e., such that both perfusion and fed-batch occurred in the same bioreactor). Through the optimization of perfusion process (e.g., specific perfusion rate (SPR)), the cell density reached over $100 \times 10^6$ cells/mL on day 8. The SPR was maintained at a range of about 0.15 to 0.05, to keep the cells in a stable and healthy condition. This led to a more than 100% increase of cell growth rate, as compared to the initial perfusion runs (Experiment #s 1 and 2). Cell density increased by about 70% per day.

Once the cell density reached over $100 \times 10^6$ cells/mL, the fed-batch process was started immediately and medium perfusion was stopped. Two to three time bolus feeds at 2 to 6% were performed every day for three days. On the second day after the fed-batch process was started, the cell density reached $119.5 \times 10^6$ cells/mL and 98% viability was achieved. Continuous feeding of glucose and/or other nutrients was performed throughout the fed-batch process to maintain glucose level and control the osmolality increase rate. The total feed volume percentage was about 60%.

Figure 7:
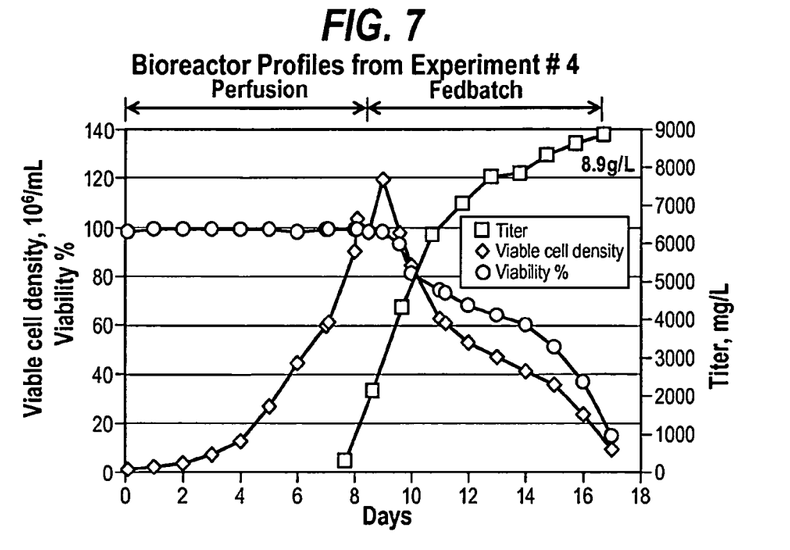
FIG. 7 is a graph showing the cell growth, cell viability and protein production profiles in production bioreactor for Experiment 4.

Optimization of concentrations and ratios for feed components led to a clear solution in the pump tubing during continuous feeding process. No visible precipitation was observed. However, feed volume increased significantly compared to experiment #2, which resulted in a diluted product concentration. As shown in FIG. 7, the final volumetric productivity was 8.9 g/L.

F. Summary of Experiments 1-4

Figure 8:
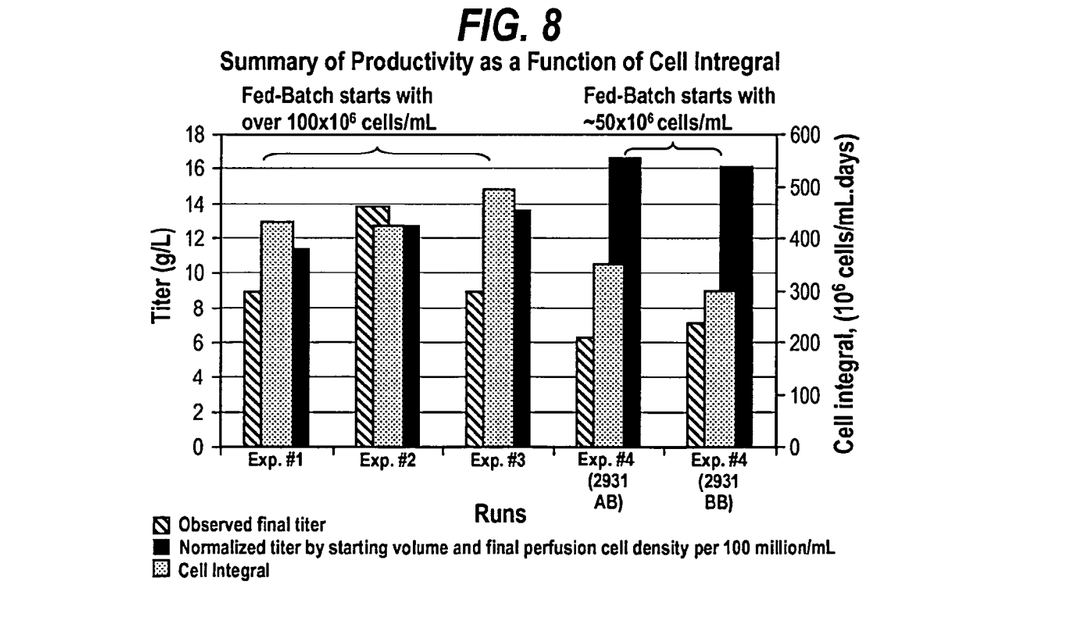
FIG. 8 is a graph summarizing the productivity results of all four Experiments as a function of cell integral.

FIG. 8 summarizes the productivity and cell integral of Experiment #s 1-3 (i.e., wherein the fed-batch process started with over $100 \times 10^6$ cells/mL) and Experiment #4 (i.e., wherein the fed-batch process started with about $50 \times 10^6$ cells/mL). The productivity is represented in terms of the actual observed final titer, as well as a normalized titer (e.g., normalized by starting volume and final perfusion cell density per 100 million cells/mL). For example, the normalized titer can be calculated as follows:

Normalized titer=observed titer/(starting culture volume x final perfusion cell density in $10^6$ cells/mL)×100

G. Optimizing Cell Culture Conditions

Various experimental parameters can be adjusted to optimize the cell culture conditions. For example, the basal medium can be optimized by concentrating the nutrients, so as to potentially reduce the perfusion volume. Alternatively or additionally, the pH buffering component in the basal medium can be optimized to handle low pH conditions typical of traditional stir tank bioreactors. Further, the feed composition and/or the feeding strategy can be optimized to promote productivity and efficiency, while maintaining good solubility.

Example 2

Clarification of Super Density Fed-Batch Cell Culture Process

Due to the super high cell densities produced in the above-described culture methods, the resultant culture has a high percentage of cell-bed solid volume (e.g., 20% cell bed volume for cultures when cell density is over $100 \times 10^6$ cells/mL by natural settling or centrifugation) and very turbid supernatant. As such, it can be challenging to harvest the protein. Accordingly, several different experimental methods were tested to improve the efficiency of the harvesting process, i.e., cell settling, filter aid, adding $CaCl_2$, decreasing the pH to 5.5 before cell settling, as well as various combinations of these techniques.

Figure 9:
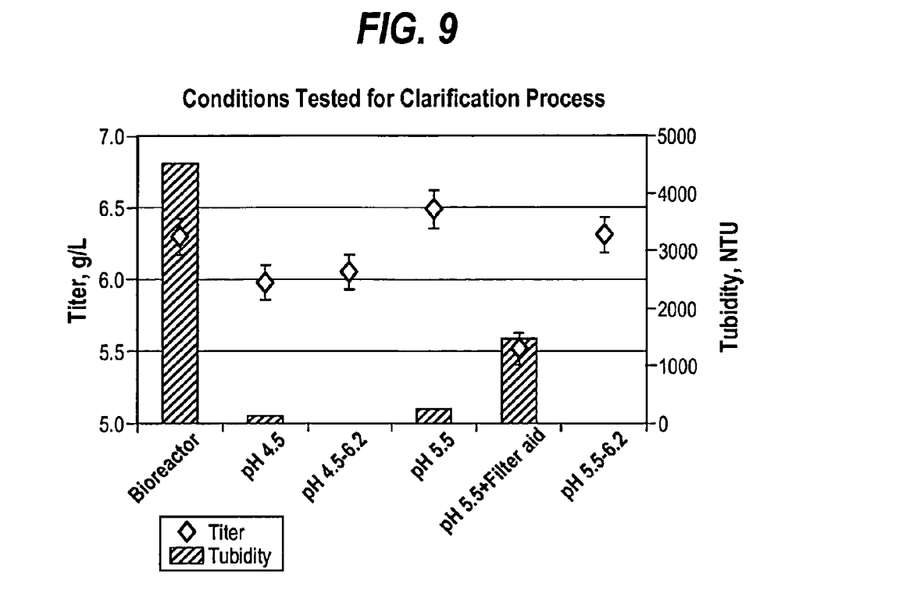
FIG. 9 is a graph depicting the effect of varying experimental parameters (i.e., pH, filter aid, etc.) on the clarification process.

Specifically, various conditions were tested using the 1201-09-29311AB run from Experiment #3 (described above). As shown in FIG. 9, the pH was decreased to 4.5 or 5.5, with or without adding filter aid, before settling the cell culture for 90 minutes. All conditions tested significantly reduced the turbidity (depicted as bars in FIG. 9) after cell settling. Compared to the control bioreactor titer, a pH 4.5 in combination with filter aid led to some product loss by protein A HPLC assay (depicted as diamond symbols in FIG. 9).

Additionally, decreasing the pH or adding calcium salts and/or filter aid prior to settling, the cell bed volume increased to about 40-50% and produced a much clearer cell supernatant. This enhanced clarification process was also tested for other proteins and similar results were obtained. In sum, a low pH settling strategy increased filtration capacity significantly and also increased the quality of the filtrate.

Figure 10:
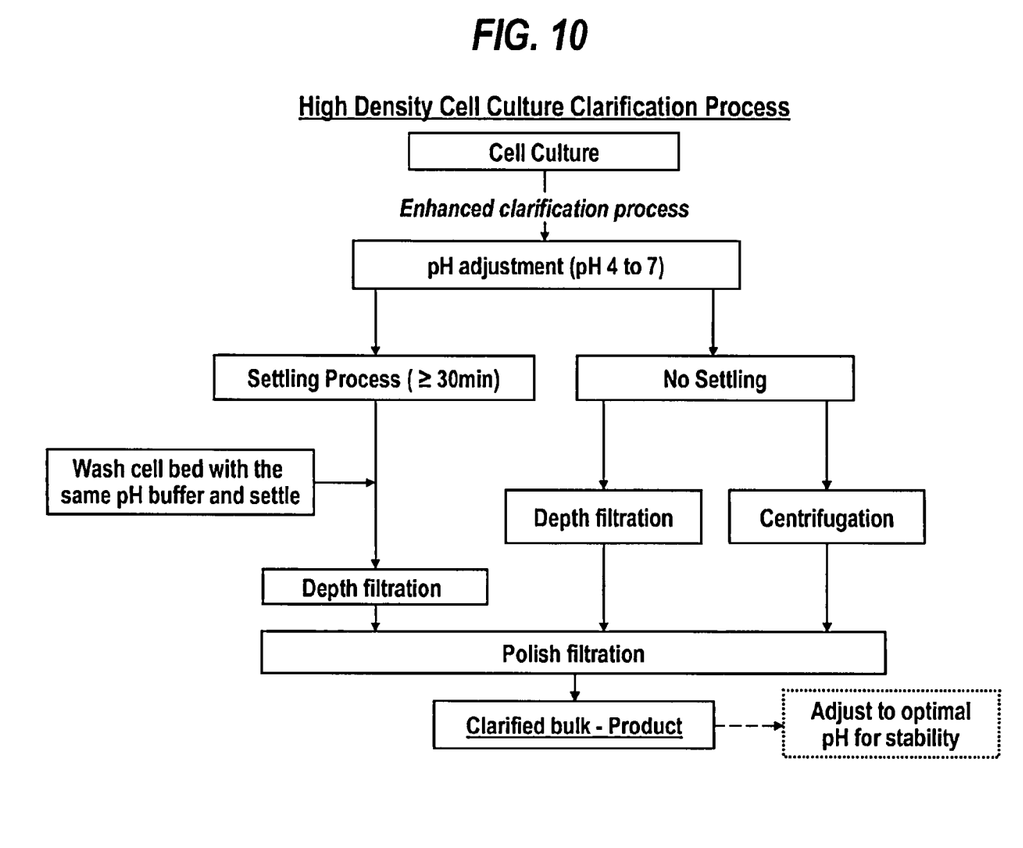
FIG. 10 is a schematic depicting the key steps in the clarification process, as well as optional techniques for enhancing the clarification process.

Additional steps, such as washing the bed with product compatible buffer or diluted PBS at the same pH condition that used to settle the cells, additional settling, and additional filtration, can optionally be performed to enhance the clarification process, as shown in FIG. 10. However, it is to be noted that FIG. 10 is not intended to be limiting, and the additional optional steps (e.g., filtration, centrifugation, washing, etc.) can occur in a different order than is depicted in FIG. 10. For example, centrifugation can optionally be performed prior to or after the settling process.

EQUIVALENTS

Those skilled in the art will recognize, or be able to ascertain using no more than routine experimentation, many equivalents of the specific embodiments of the invention described herein. Such equivalents are intended to be encompassed by the following claims. Any combination of the embodiments disclosed in the dependent claims is contemplated to be within the scope of the invention.

INCORPORATION BY REFERENCE

The contents of all references, patents and published patent applications cited throughout this application, as well as the figures and Sequence Listing, are expressly incorporated herein by reference.

We claim:

1. A method of increasing production of a protein in a cell culture, comprising:
 a) growing cells which produce the protein in a perfusion cell culture to a cell density of at least about $100 \times 10^6$ cells/mL; and
 b) transferring the cells to a fed-batch cell culture, such that the cells enter a production phase, thereby increasing production of a protein in the cells.

2. The method of claim 1, wherein the cells are grown in the perfusion cell culture to a cell density of between about $100 \times 10^6$ cells/mL and $200 \times 10^6$ cells/mL.

3. The method of claim 1, wherein the cells are animal cells.

4. The method of claim 1, wherein the protein is an antibody.

5. The method of claim 1, wherein the protein is selected from the group consisting of enzymes, receptors, fusion proteins, cytokines, regulatory factors, hormones, antigen-binding agents, therapeutic proteins, and diagnostic proteins.

6. The method of claim 1, wherein the perfusion cell culture and fed-batch cell culture are grown in a single bioreactor.

7. The method of claim 1, wherein the perfusion cell culture and fed-batch cell culture are grown in separate bioreactors.

8. The method of claim 1, wherein the fed-batch cell culture is grown in multiple bioreactors.

9. The method of claim 1, further comprising collecting the protein from the fed-batch cell culture and not the perfusion cell culture.

10. The method of claim 1, further comprising collecting the protein from both the perfusion culture and the fed-batch cell culture.

11. The method of claim 1, wherein the cells are Chinese Hamster Ovary (CHO) cells.

12. The method of claim 4, wherein the antibody is a monoclonal antibody.

13. The method of claim 12, wherein the monoclonal antibody is selected from the group consisting of a human, humanized and chimeric antibody.

\* \* \* \* \*